United States Patent
Goto et al.

(10) Patent No.: US 6,906,795 B2
(45) Date of Patent: Jun. 14, 2005

(54) METHOD AND APPARATUS FOR EXAMINING FOREIGN MATTERS IN THROUGH HOLES

(75) Inventors: Noboru Goto, Yamagata-ken (JP); Mikio Saito, Yamagata-ken (JP)

(73) Assignee: Seiko Epson Corporation (JP)

( * ) Notice: Subject to any disclaimer, the term of this patent is extended or adjusted under 35 U.S.C. 154(b) by 482 days.

(21) Appl. No.: 09/821,789

(22) Filed: Mar. 29, 2001

(65) Prior Publication Data

US 2002/0051563 A1 May 2, 2002

(30) Foreign Application Priority Data

Apr. 27, 2000 (JP) ........................................ 2000-127804

(51) Int. Cl.⁷ ............................................. G01N 21/00
(52) U.S. Cl. ................................................... 356/237.6
(58) Field of Search .......................... 356/237.1–237.6, 356/388–391, 431–433, 623; 382/147–152; 250/330, 358.1, 342, 305–310

(56) References Cited

U.S. PATENT DOCUMENTS 6,360,005 B1 * 3/2002 Aloni et al. ................ 382/148

FOREIGN PATENT DOCUMENTS

JP 61-256237 11/1986

OTHER PUBLICATIONS

U.S. Appl. No. 09/821,695, filed Mar. 29, 2001, Goto et al.
U.S. Appl. No. 09/821,816, filed Mar. 29, 2001, Goto et al.
Notification of Reasons of Rejection (in Chinese and Japanese).

* cited by examiner

Primary Examiner—Tu T. Nguyen
(74) Attorney, Agent, or Firm—Harness, Dickey & Pierce, P.L.C.

(57) ABSTRACT

A method and an apparatus for examining foreign matters in through holes includes a light source provided on one side and a line sensor camera provided on the other sides, whereby the light source and sensor camera cooperate to inspect a work piece having a plurality of through holes. A parallel displacement system is provided to translate the work piece and the line sensor camera relative to each other to allow the line sensor camera to detect light passing through the plurality of through holes in one lot. An image processing device and determination device are also provided to determine whether foreign matters are present in the through holes based on deviations among receiving light regions corresponding to the respective through holes.

5 Claims, 14 Drawing Sheets

Fig. 4 (1)
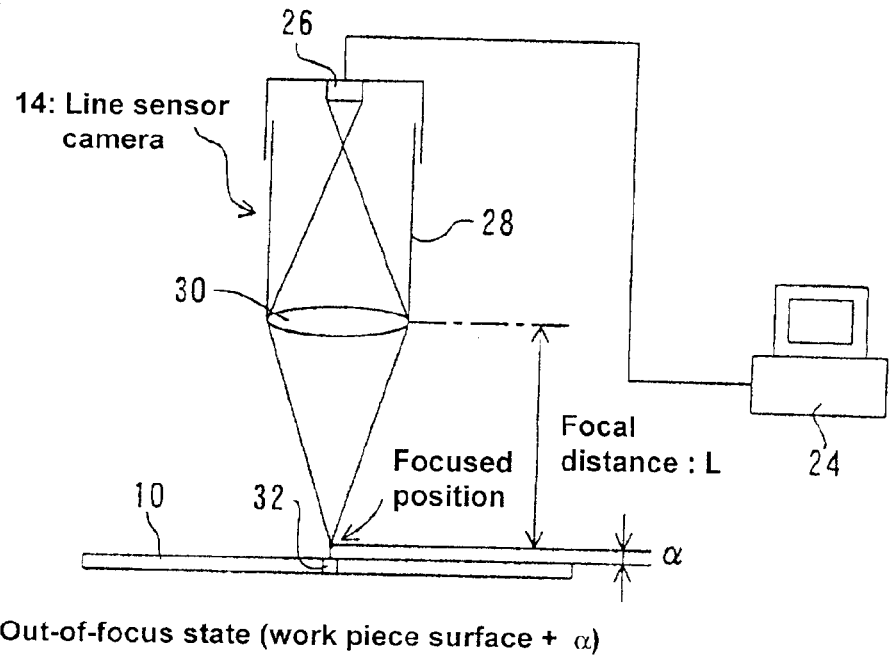
Out-of-focus state (work piece surface + α)
Fig. 4 (2)
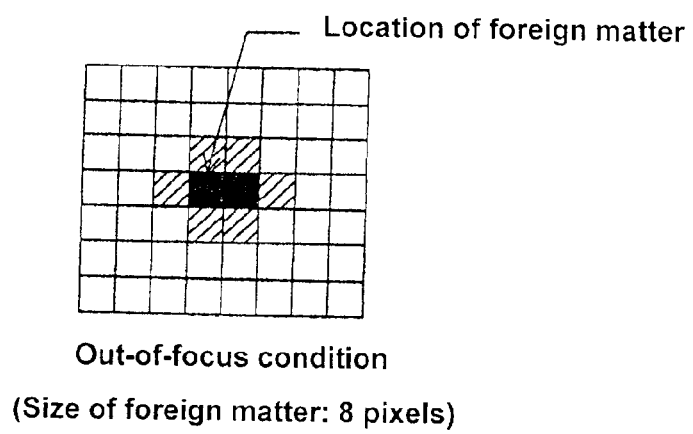
Out-of-focus condition
(Size of foreign matter: 8 pixels)

Fig. 5 (1)
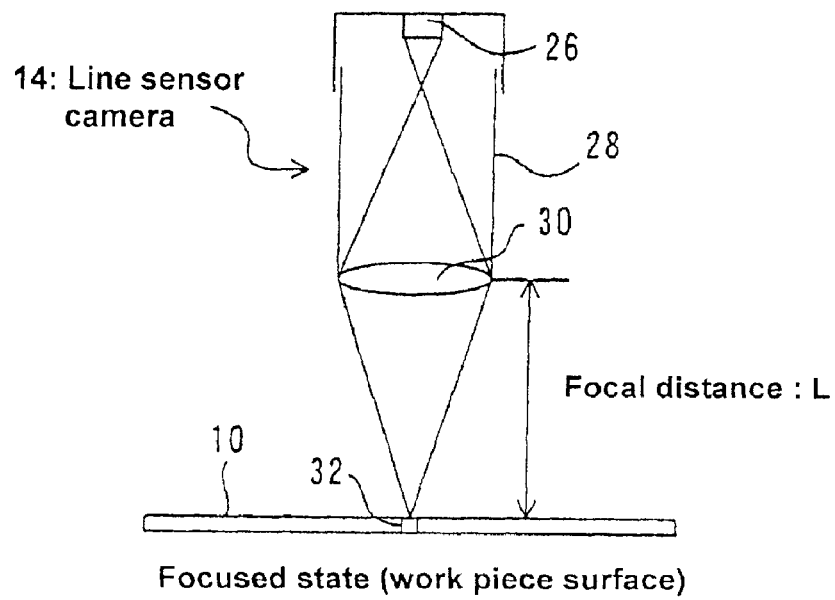
Focused state (work piece surface)
Fig. 5 (2)
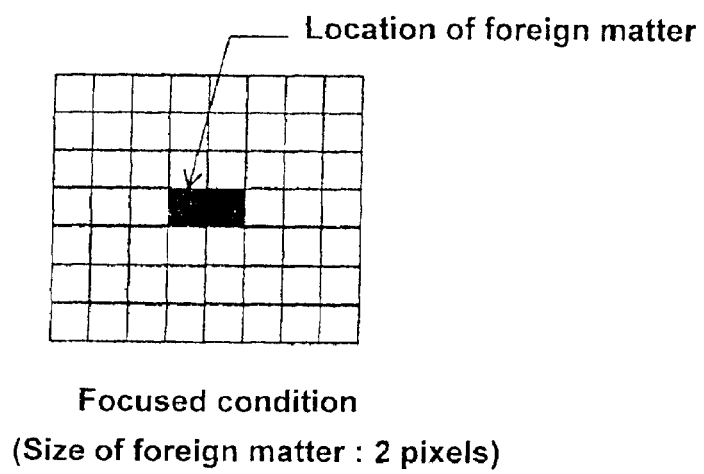
Focused condition
(Size of foreign matter : 2 pixels)

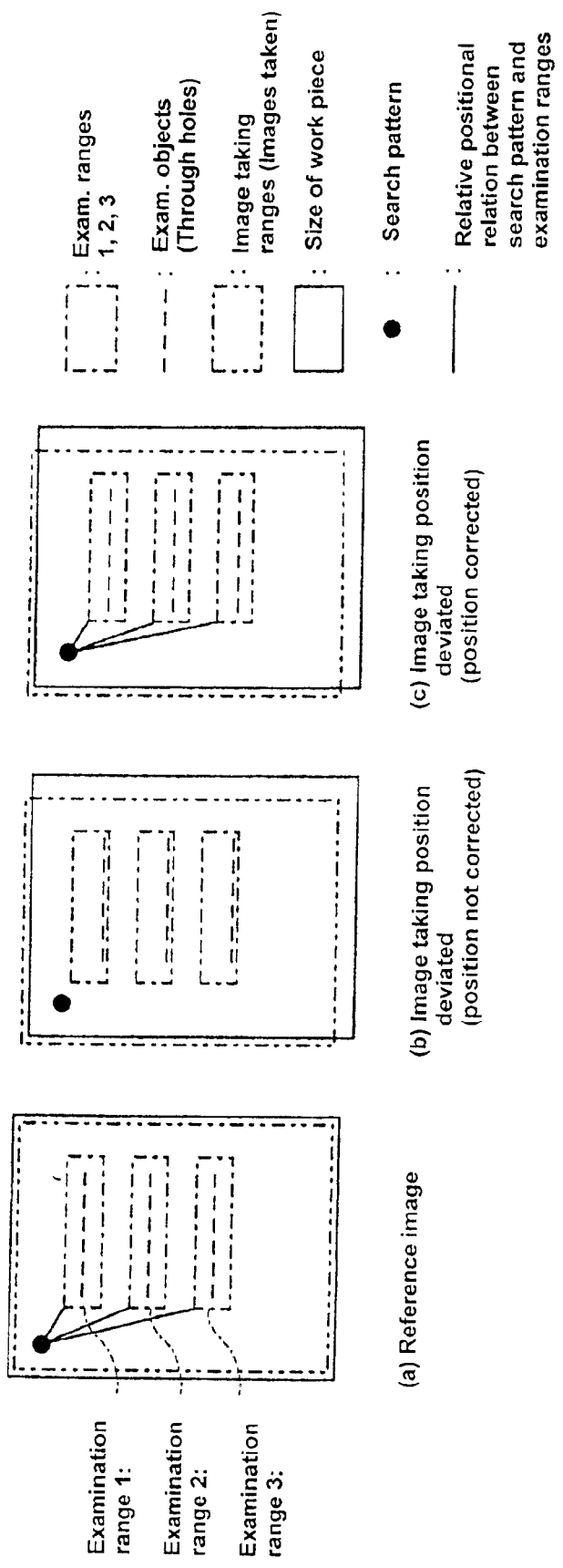

Fig. 8 (1)
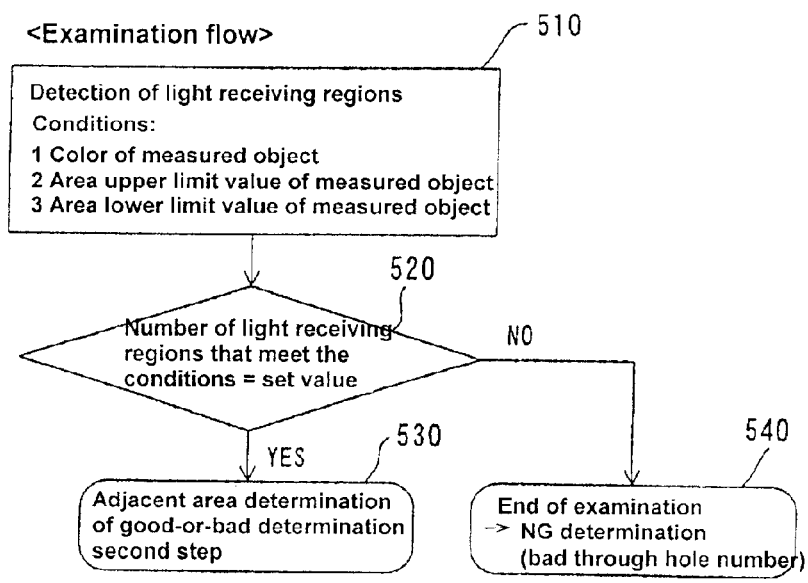
Fig. 8 (2)
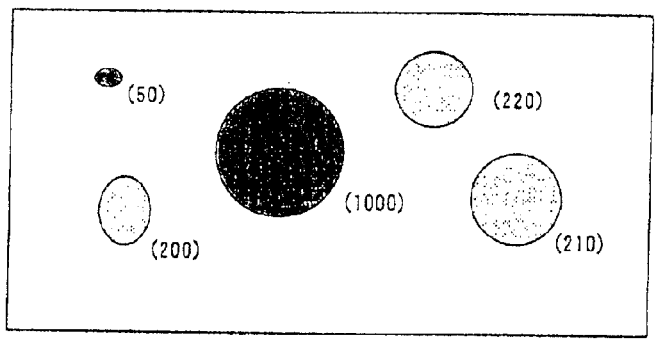

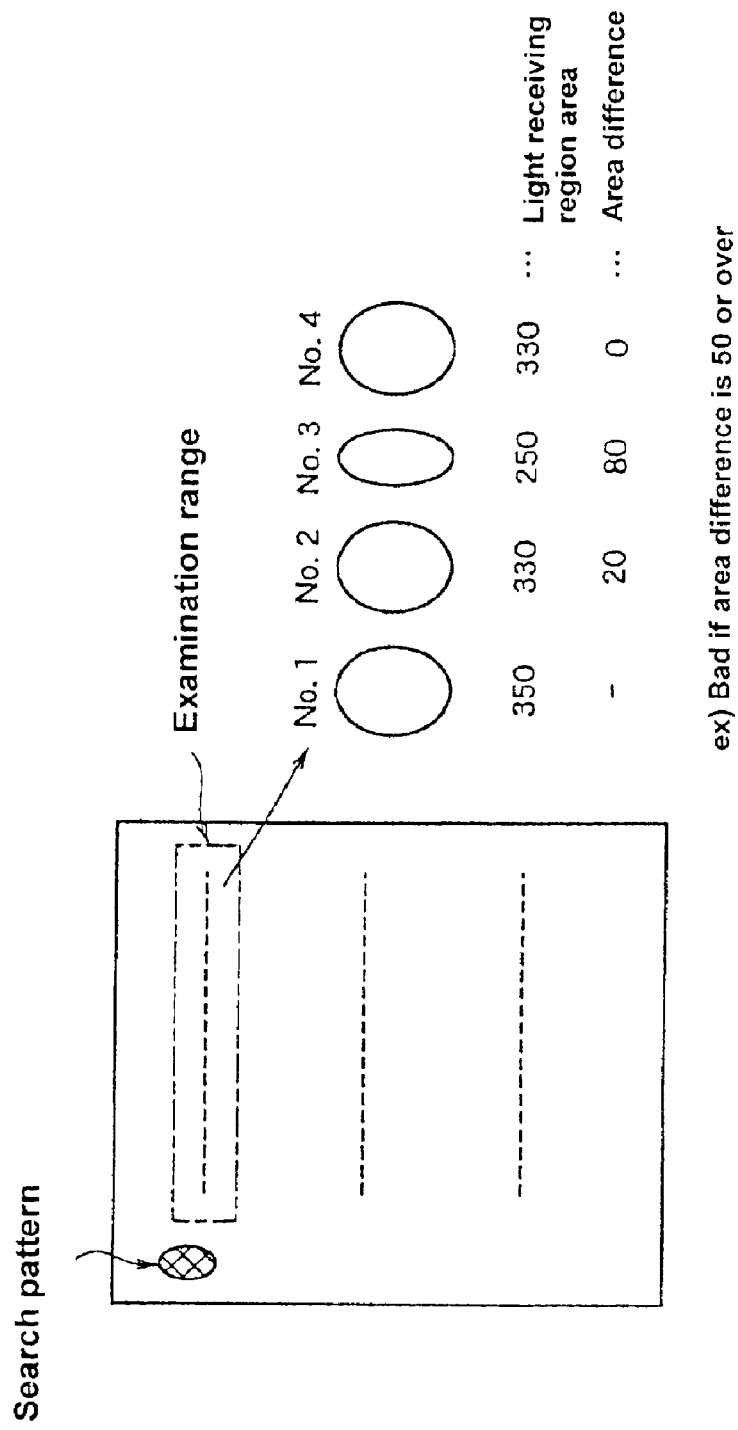

<<Flow of adjacent area determination>>

<<Flow of adjacent area determination process and Examination of each examination range>>

Fig. 13 (1)
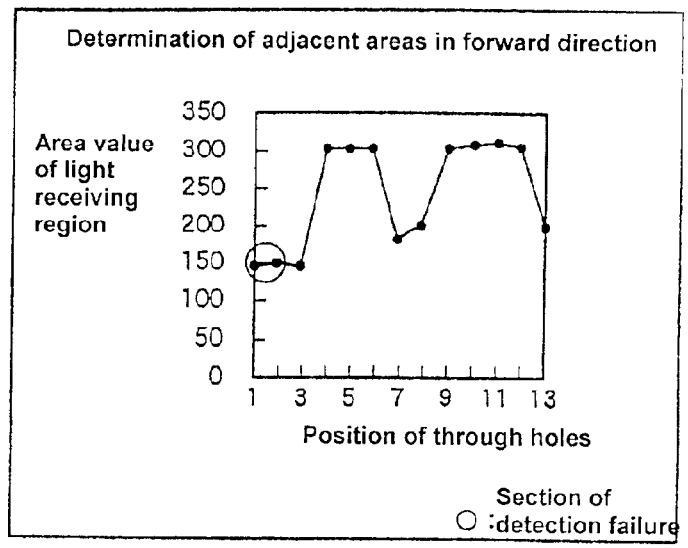
Fig. 13 (2)
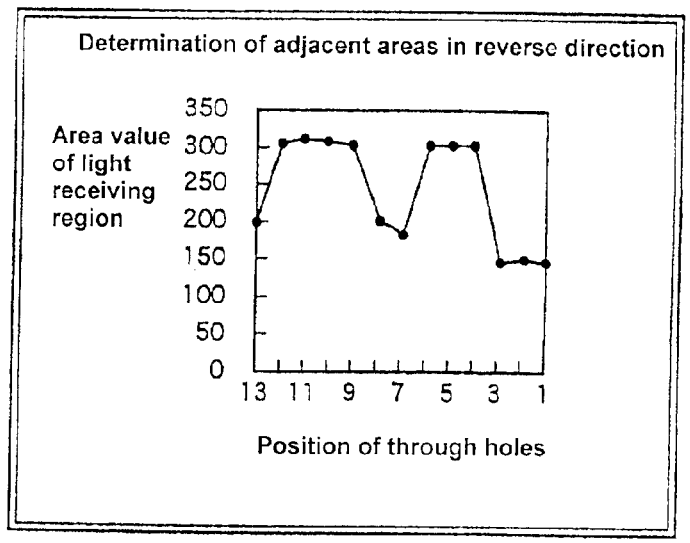

5: Z-axis automatic control function

Work piece with a plurality of through holes

Image taken (for one throgh hole)

METHOD AND APPARATUS FOR EXAMINING FOREIGN MATTERS IN THROUGH HOLES

TECHNICAL FIELD

The present invention relates to a method and an apparatus for examining foreign matters in through holes, and more particularly to a method and an apparatus that are suitable for examining the presence or the absence of foreign matters in through holes each having a diameter of several ten micron millimeters.

BACKGROUND TECHNOLOGY

Examinations are generally conducted on through holes each having a diameter of several ten~several hundred micron millimeters to check if a correct number of the through holes are opened, if any foreign matters are present in the through holes, and the like. Optical methods are generally conducted for such examinations. For example, an area sensor camera is used to photograph an examining surface of a work piece where through holes are formed, and an image processing apparatus is used to compare the result with a reference value to make a determination as to whether or not the result is good. However, in the conventional example described above, beside the image processing apparatus, an auto-focusing unit, a microscope, and electron beams are required, whereby the examination is conducted for each one of the through holes, or with an expanded image that is expanded at a high level of magnification.

In a general structure of this type of examination apparatus, as shown in FIG. 14, a work piece 1 having through holes is disposed at a fixed position, a light source 2 is disposed on a lower side thereof and an image taking device that integrates a microscope unit 3 and an area sensor camera 4 is disposed on an upper side thereof. The image taking device can be elevated or lowered by a Z-axis automatic control system 5, and the area sensor camera 4 is connected to an image processing apparatus 7 through an automatic focusing unit 6. The examination apparatus is used to photograph the work piece having a plurality of through holes 8 as shown in FIG. 15. An image is taken for every one of the through holes 8 as one unit, and a comparing process to compare a pixel area of a reference through hole and a pixel area of a measured through hole is conducted to determine as to whether the through hole is good or bad. For example, when a foreign matter is present in the through hole 8, the amount of the passing light is reduced, and therefore the measured pixel area becomes smaller, such that the through hole 8 having a pixel area that is below a specified threshold value is determined as being defective.

However, the conventional method described above has the following problems. When the number of through holes increases, it takes too long to conduct the examination. When a highly magnified image is to be taken, demands for mechanical precision of the apparatus become stricter, and therefore its manufacturing cost becomes higher. In other words, because the depth of focus becomes narrower, the automatic focusing unit 6, the automatic-control system for camera's z-axis 5, and the like are required. Also, because the range of field of view becomes narrower, the table on which the work piece 1 is mounted requires a high positioning accuracy.

Furthermore, when foreign matters in through holes are examined by the photographing method using the conventional area sensor camera, the number of pixels is limited and therefore its resolving power is limited. In particular, when foreign matters are light-transmissive, their recognition is extremely difficult, and therefore there are possibilities to erroneously detect good products as bad products.

The present invention focuses on the problems of the conventional art described above, and it is an object of the present invention to provide a method and an apparatus for examining foreign matters in through holes, which can quickly make determinations with low costs and high accuracy.

DESCRIPTION OF THE INVENTION

To achieve the object described above, the present invention is characterized in that light passing through a plurality of through holes having a uniform size is taken as image data by a relative translation movement of a line sensor camera, and sizes of regions that receive the individual passing light of the image data are mutually compared to determine presence or absence of foreign matters.

By using a line sensor in the above structure, a wide range of images can be taken in, and determinations at a high resolving power can be performed. Also, a plurality of through holes can be processed in one lot, the number of image taking operations and the number of shifts of the table can be reduced, such that the cycle time can be shortened. Furthermore, since an image is not taken for each of the through holes, the positioning accuracy for the table when the image is taken may not require to be so high, and an automatic focusing function with a higher amplification may not be required, such that the apparatus can be designed with excessive functions being omitted. Similarly, the examination cycle can be shorted by the use of a line sensor camera.

Also, in accordance with the present invention, the present invention may be constructed such that light transmitted through a plurality of through holes having a uniform size is taken as image data in the unit of an individual through hole or in the unit of a group consisting a plurality of the through holes by an area sensor camera, and sizes of light receiving regions that correspond to the respective through holes in the image data are mutually compared with one another to determine presence or absence of foreign matters.

In the cases described above, the present invention may be constructed such that, after counting and determining the number of the areas of light receiving regions corresponding to the through holes, the areas of light receiving regions are mutually compared, or the areas of light receiving regions are labeled and the labeled areas of light receiving regions are mutually compared to determine presence or absence of foreign matters.

Also, a method for examining foreign matters in through holes in accordance with the present invention may be composed such that light transmitted through a plurality of through holes having a uniform size is taken as image data by a relative translation movement of a line sensor camera, and sizes of regions that receive the individual passing light in the image data are mutually compared based on magnitudes of differences in light receiving regions of adjacent ones of the through holes to determine presence or absence of foreign matters.

Also, a method for examining foreign matters in through holes in accordance with the present invention may be composed such that the examination is conducted by imaging with an imaging focal point of the line sensor camera or the area sensor camera being shifted with respect to a surface of the work piece.

Also, a method for examining foreign matters in through holes in accordance with the present invention may be composed such that the imaging is conducted with an imaging focal point of the line sensor camera or the area sensor camera being shifted with respect to a surface of the work piece to thereby expand an image area of the passing light.

An apparatus for examining foreign matters in through holes in accordance with the present invention may comprise a light source provided on one side and a line sensor camera provided on the other side with a work piece having a plurality of through holes being placed between them, a parallel displacement system that translates the work piece and the line sensor camera relative to each other to allow the line sensor camera to detect light passing through the plurality of through holes in one lot, and an image processing device that receives imaging signals provided by the line sensor camera to obtain a plurality of binary image data corresponding to the plurality of through holes in the work piece, wherein the image processing device is equipped with a determination device that makes a determination as to whether foreign matters are present or absent in the through holes based on deviations among receiving light regions corresponding to the respective through holes.

Furthermore, the present invention may comprise a light source provided on one side and an area sensor camera provided on the other side with a work piece having a plurality of through holes being placed between them, a parallel displacement system that translates the work piece and the area sensor camera relative to one another to allow the area sensor camera to detect light passing through each individual one of the plurality of through holes or through the plurality of through holes in one lot, and an image processing device that receives imaging signals provided by the area sensor camera to obtain a plurality of binary image data corresponding to the plurality of through holes in the work piece, wherein the image processing device is equipped with a determination device that makes a determination as to whether foreign matters are present or absent in the through holes based on deviations among receiving light regions corresponding to the respective through holes.

Also, an apparatus for examining foreign matters in through holes in accordance with the present invention may be composed such that relative positions of the sensor camera and the surface of the work piece are set such that an imaging focal point of the line sensor camera or the area sensor camera is shifted from the surface of the work piece.

Also, an apparatus for examining foreign matters in through holes in accordance with the present invention may be composed such that relative positions of the sensor camera and the surface of the work piece are set such that an imaging focal point of the line sensor camera or the area sensor camera is shifted from the surface of the work piece, whereby imaging is conducted with an image area of the passing light being expanded.

BRIEF DESCRIPTION OF THE DRAWINGS

FIGS. 5(1), 5(2) shows a principle of an ordinary imaging and an example of a photographed image of light passing through a through hole.

FIG. 7 is an illustration to describe pattern matching.

FIG. 8(1), 8(2) shows a flow chart of an examination of the number of light receiving regions and an example of measured images.

FIG. 9 is an illustration to describe a photographed image of a work piece.

FIG. 13(1), 13(2) shows graphs of relations between through hole locations and through hole area values in examined results in a forward direction and a reverse direction.

BEST MODE EMBODIMENTS OF THE PRESENT INVENTION

A method and an apparatus for examining foreign matters in through holes in accordance with an embodiment of the present invention are described in detail with reference to the accompanying drawings.

Figure 1:
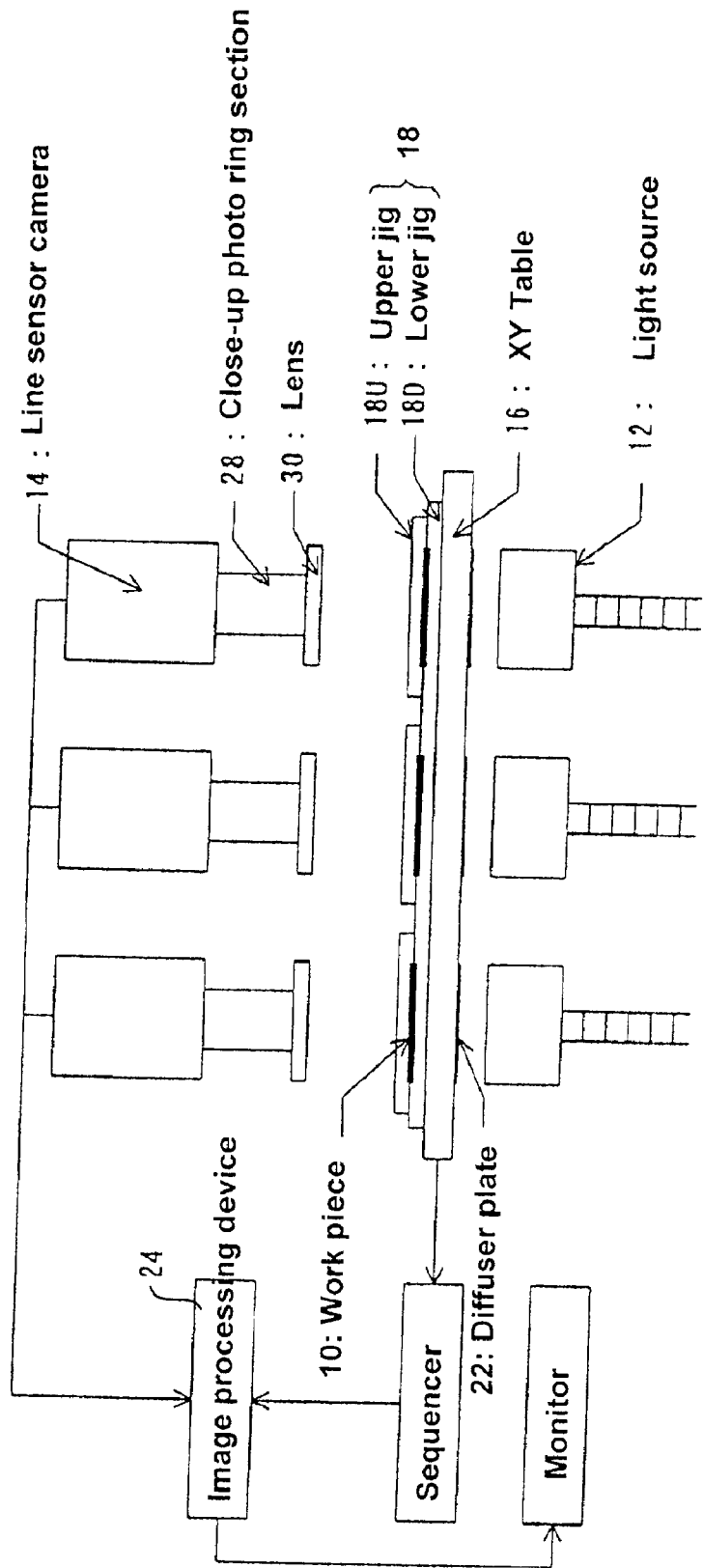
FIG. 1 shows a composition of an apparatus for examining foreign matters in through holes in accordance with one embodiment of the present invention.
Figure 2:
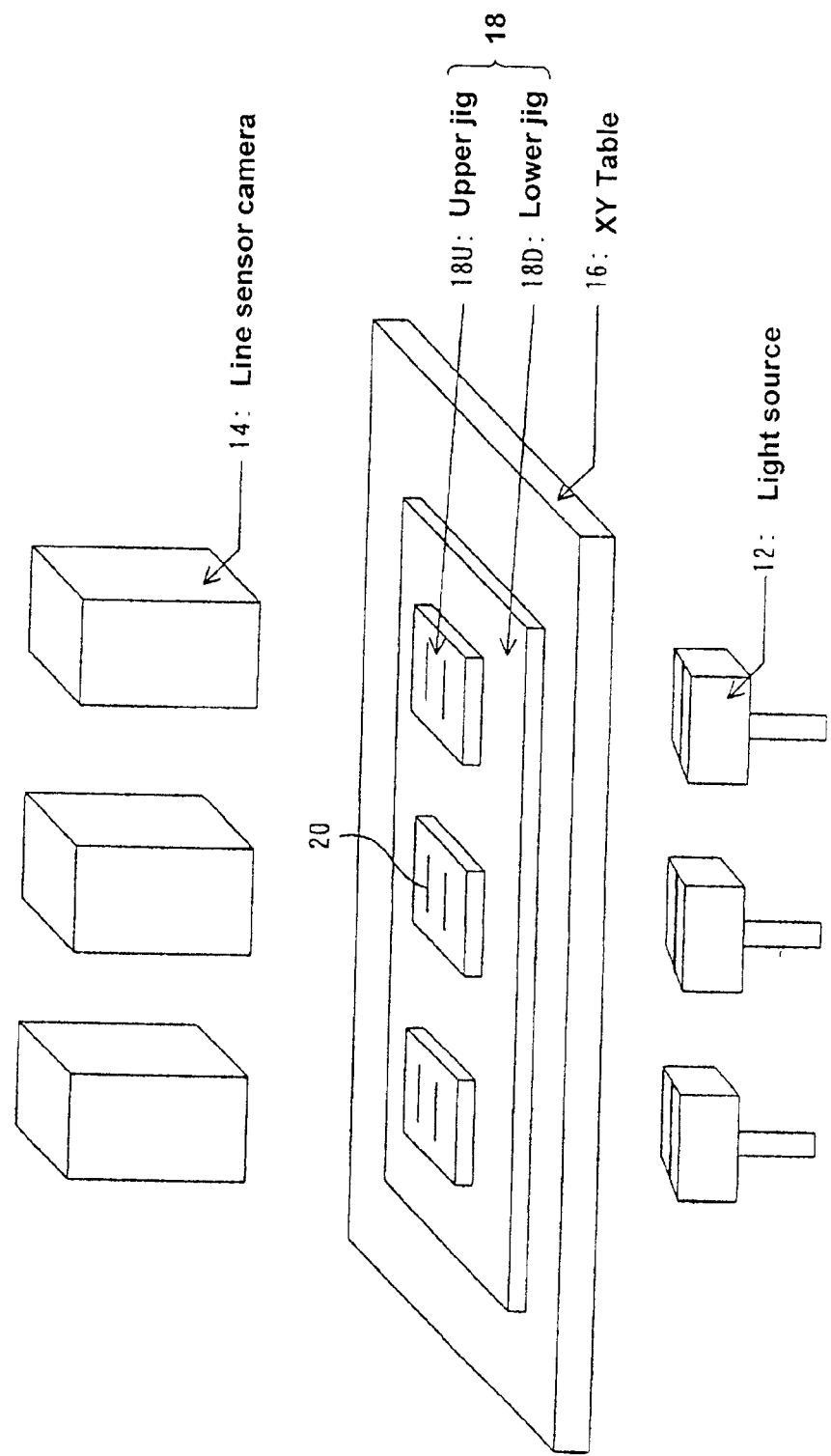
FIG. 2 shows a perspective view of a main portion of the apparatus.
Figure 3:
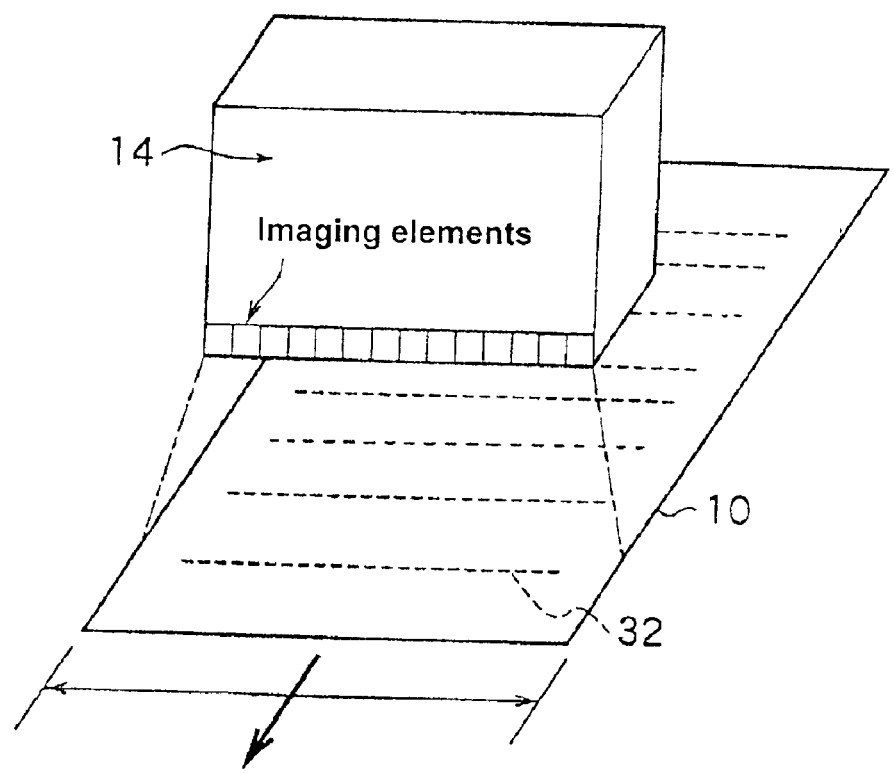
FIG. 3 shows a relation between a line sensor camera used in the apparatus of the present embodiment and a work piece FIGS. 4(1), 4(2) shows a principle of imaging by the apparatus of the preset embodiment and an example of a photographed image of light passing through a through hole.

FIG. 1 shows a block diagram of a structure of a through hole examination apparatus in accordance with one embodiment of the present invention. FIG. 2 shows a perspective view of components of a main part of the apparatus. As shown in these figures, in principle, a light source 12 is disposed below a lower surface of a work piece 10 in a plate shape having a plurality of through holes arranged in columns, and light is irradiated toward the through holes from the rear side of the work piece 10. On the other hand, a line sensor camera 14 having a plurality of imaging elements such as CCD elements or C-MOS semiconductor elements is disposed above an upper surface of the work piece 10, and light passing through the through holes is imaged by the line sensor camera 14. Therefore, the work piece 10 is irradiated with light by the light source 12 disposed on one plane side of the work piece 10, and an image is taken by the line sensor camera 14 that is disposed on the opposite side of the light source 12 across the work piece 10. As shown in FIG. 3, the line sensor camera 14 and the light source 12 are translated relative to the work piece 10 to take plane images of the passing light. Detection of foreign matters is conducted using the following characteristic. When there is a foreign matter in a through hole, light is blocked by the foreign matter, and an area value representative of the light receiving region becomes smaller. In one embodiment, the line sensor camera 14 takes an image with about 5000 pixels for the width of the field of view. By the use of the line sensor camera 14, a higher resolving power is obtained to the extent that the resolving power per one pixel can be improved to about 3 $\mu$m. It is noted that the example shown in the figure simultaneously examines three work pieces 10. Accordingly, the light sources 12 and the line sensor cameras 14 are provided in three pairs. However, the examination can be conducted with one unit.

The line sensor camera 14 may be translated relative to the work piece 10 to take plane images. As shown in FIGS. 1 and 2, in accordance with the present embodiment, the work piece 10 is mounted on an XY table 16, and moved for scanning in a direction perpendicular to the columns of the imaging elements.

A fixing jig 18 is used to clamp the work piece 10 to place the work piece 10 at a predetermined fixed position on the XY table 16. The fixing jig 18 is formed from a lower jig 18D and an upper jig 18U, and is positioned and affixed at a specified location on the table by an appropriate fixing device. Slits 20 corresponding to the columns of the through holes of the work piece 10 are formed in the fixing jig 18, such that light is transmitted through the slits 20 and taken by the line sensor camera 14. Also, the light source 12 disposed below a lower surface of the XY table 16 is formed from a line-like lighting. Further, a diffuser plate 22 is mounted on a lower surface of the table to mitigate irregularities in the light intensity of light emitted from the light source 12 so that the light is uniformly irradiated on the columns of the through holes.

By the structure described above, the work piece 10 is moved by the XY table 16, and light passing through the column of the through holes is received by the line sensor camera 14 to take an image. Data representative of the image is inputted in an image processing device 24, and a determination device built in the image processing device 24 determines the presence or the absence of foreign matters in the through holes. When an image is taken, a determination can be difficult if a foreign matter is light transmissive. In accordance with the present embodiment, the position of the focal point of the line sensor camera 14 is not concurred with the surface of the work piece 10, but is set at a position shifted from the surface of the work piece. In other words, the line sensor camera 14 is positioned at a distance (L+α) from the through hole of the work piece 10, which is longer than a focal length L, in order to apparently expand the area of the photographed image of the passing light.

An illustration of the principle is shown in FIG. 4, and a comparison example is show in FIG. 5. First, the line sensor camera 14 is equipped with a sensor main body 26 in which a plurality of CCD elements are linearly arranged, a close-up photographing ring section 28 and an optical lens 30 (see FIG. 4). In general, as shown in FIG. 5(1), the close-up photographing ring 28 is adjusted such that the sensor camera is set at a position (at a focal distance L) with its focal point being concurred with a plane of an opening of the through hole 32 formed in the work piece 10, to take in an image corresponding to the size of the opening of the through hole 32. However, in accordance with the embodiment of the present invention, the focal point is set to be located above the surface of the work piece 10 (toward the sensor side). In the photographed image under a focused condition, a region in which the passing light is blocked by a foreign matter in the through hole is detected as an area of, for example, two pixels as shown in FIG. 5(2). In contrast, in accordance with the embodiment of the present invention, as shown in FIG. 4(2), the region can be detected as an area of 8 pixels. In other words, under the focused condition, only the light passing through the opening section of the through hole 32 is detected. However, under an out-of-focus condition in accordance with the embodiment of the present invention, although the light intensity per unit area is reduced, an area value of the light receiving region in the photographed image corresponding to the through hole 32 is enlarged and an area of the foreign matter is likewise apparently enlarged. By the structure described above, a measured value, in other words, an area value of passing light amount X is defined by the following formula:

$$X=(S-\alpha)\beta,$$

where S is an area value of the received light region corresponding to the through hole 32, α is an area value of the foreign matter region, and β is an area expansion coefficient (β>1) due to the out-of-focus effect. When β=1, the focal point concurs with the surface of the work piece.

In this manner, the position of the focal point of the line sensor camera 14 is not concurred with the through hole 32 of the work piece 10 such that it is shifted from the through hole 32 of the work piece 10 to positively create an out-of-focus condition. As a result, the photographed image is apparently expanded, whereby the detection power to detect foreign matters is increased.

A detected signal from the line sensor camera 14 is inputted in an image processing device 24 that is formed from a computer, and a plurality of binary image data corresponding to a column or a specified region including the plurality of through holes 32 in the work piece 10 is obtained. The image processing device 24 is equipped with a determination device that performs a determination process to count the number of light receiving regions corresponding to the respective through holes 32 based on the binary image data and determine as to whether or not the counted number is the same as a set value, and a determination process to compare adjacent areas to make a determination as to whether or not foreign matters are present.

Figure 6:
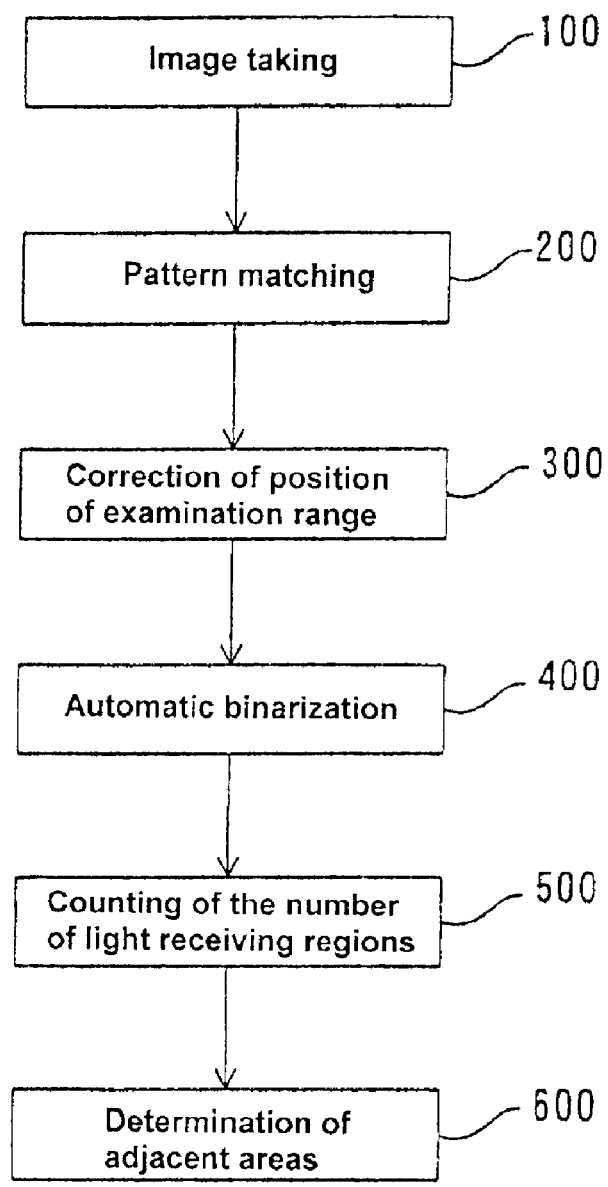
FIG. 6 shows a flow chart of a process by the apparatus of the present embodiment.

FIG. 6 shows a flow chart of a series of the processes described above. More specifically, the image processing device 24 equipped with the determination device takes in a region including a plurality of examination ranges in a lot as an image through the line sensor camera 14 (step 100), and performs a pattern matching for correcting positions of the examination ranges (step 200). If the pattern matching finds a positional deviation from a reference image, the position of the examination ranges is corrected (step 300), and as a pre-process prior to the examination, the taken image is subject to a binarizing process (step 400). The steps described so far are a process performed by the image processing device 24. Then, a good-or-bad determination process is performed. First, in order to confirm if the through holes are present in a specified number, each of the light receiving regions corresponding to the respective through holes 32 is recognized as one mass, and the number thereof is counted to determine if the through holes are opened in the specified number (step 500). Then, finally, a comparison process to compare adjacent areas is conducted to make a good-or-bad determination depending on the absence or the presence of foreign matters (step 600).

Next, concrete process contents of each of the steps are described. If there is a positional deviation with respect to a reference image, there is a possibility that the through holes 32 as an object to be examined may be located outside the examination range. Therefore, the pattern matching process in step 200 is conducted to correct any positional deviation with respect to the reference image at each time the examination is started, or each time an image is taken. As shown in FIG. 7 (a), a normal image taking range (two-dot and dash line) with respect to the work piece 10 is set as a reference image. Relative distances to examination ranges (dot and dash line) that enclose columns of through holes are obtained based on a search pattern (•) set on the work piece 10. When the position of an image taken deviates, as shown in FIG. 7(b), the examination ranges are moved to be consistent with the relative positions between the search pattern and the examination ranges, such that the columns of the through holes as an object to be examined are located within the examination ranges, as shown in FIG. 7 (c).

The automatic binarizing process in step 400 is a process that is ordinarily in the image processing. The line sensor camera performs this process in order to discriminate CCD elements that receive the light passing through the through holes from CCD elements that do not receive the passing light to carry out image measurements. In this process, area values and characteristic amounts are obtained. It is noted that the automatic binarizing process described herein is not intended to fix binary levels, but instead it is a function to have the binary levels automatically adjusted in order to cope with some variations in the light amount.

The image processing device 24 performs the steps described so far. Image data obtained by the above-described process is sent to the determination device in which, as the good-or-bad determination, the count process in step 500 to count the number of the light receiving regions is initially conducted, and then the adjacent area determination process is conducted in step 600. The count process to count the number of the light receiving regions compares the numbers of the light receiving regions in the examination regions that meet a given condition to determine whether or not they are in the same number. A concrete examination flow is shown in FIG. 8(1). To count the number of areas that can be recognized as the light receiving regions corresponding to the individual through holes 32, first, light receiving regions that meet the given condition are detected (step 510). The given condition includes color of an object to be measured, an area upper limit value of the object to be measured, and an area lower limit value of the object to be measured. The color of the object to be measured is binarized, and therefore "white" or "black" is selected. When an area value exceeds the area lower limit value and the area upper limit value, such area value is not recognized as a light receiving region.

For example, as shown in FIG. 8(2), when five candidate light receiving regions are detected, and they have area values with the numbers indicated in parentheses. When the area lower limit value is 100 and the area upper limit value is 800, the number of the light receiving regions that meet this condition is three "3". When the light receiving regions that meet the condition are detected, the detected number and a set value are compared (step 520). The set value is a prescribed value of the number of through holes that are to be enclosed in the examination region. When the number of the through holes concurs with the prescribed number, the process proceeds (in step 530) to the adjacent area determination process (step 600). When it does not concur with the prescribed number, the number of through holes is determined to be defective and an examination ending process is conducted (step 540).

The light receiving region count process functions as a countermeasure against detection failures in the following adjacent area determination, can also be used to determine the type of an object work piece to be examined, and can further avoid waste in the image processing process. In other words, the determination process mutually compares adjacent through holes (step 600). There is a risk that a foreign matter detection failure may occur. Namely, when all of the light receiving regions in the examination range are bad, all mutually compared values (area value differences) may become small, such that they cannot be determined as bad through holes. However, by performing the counting and determination of the number of light receiving regions prior to such a process, the occurrence of detection failures can be prevented. Also, a plurality of examination ranges can be set, and the number of light receiving regions (through holes) can be set individually for each of the examination ranges as a unit. Therefore, depending on combinations of the examination ranges in an image taken, the type of the work piece can be readily determined. For example, discriminations can be made among a work piece with three examination ranges and the number of set light receiving regions (through holes) in each of the examination ranges being 50, 50, 50, a work piece with three examination ranges and the number of set light receiving regions being 30, 30, 30, and a work piece with two examination ranges and the number of set light receiving regions being 30, 20. Furthermore, when the number of the light receiving regions does not concur with the set value, a process to stop the examination of the work piece is conducted (step 540). As a result, the processing load in the image processing device 24 is alleviated, and therefore the processing time can be shortened.

After the light receiving region count process is completed, the adjacent area determination process in step 600 is successively conducted. In this process, each of the light receiving regions is not compared with the reference area values (the upper limit value and the lower limit value). Instead, an area difference between adjacent light receiving regions corresponding to adjacent ones of the through holes 32 is obtained, and a good-or-bad determination is made depending on whether the area difference is greater than a specified area difference. Namely, an area of each of the light receiving regions corresponding to the respective through holes in each of the examination ranges in the image taken is obtained. For example, as shown in FIG. 9, they are obtained as No. 1: 350, No. 2: 330, No. 3: 250, No. 4: 330, . . . , . . . , and so forth, and differences among the detected areas of the light receiving regions are calculated. When the area difference is within a reference value, the target through holes are renewed by one and an area difference between them is obtained. When the area difference exceeds the reference value, the one with a larger diameter is taken as a reference and is compared with the measured area of the next light receiving region. For example, when the reference value of an area difference is "50", an area difference between No. 1 and No. 2 is "−20", which is acceptable. Then, the through holes are renewed by one, and an area difference between No. 2 and No. 3 is obtained. In this case, the difference is "80", which exceeds the reference value. Accordingly, No. 2 with a larger area is accepted, and No. 3 with a smaller area is determined as unacceptable. No. 2 is taken as the next target through hole, and is compared with No. 4. Good-or-bad determination can be made in this manner using the fact that the presence of a foreign matter reduces the area of a light receiving region.

Figure 10:
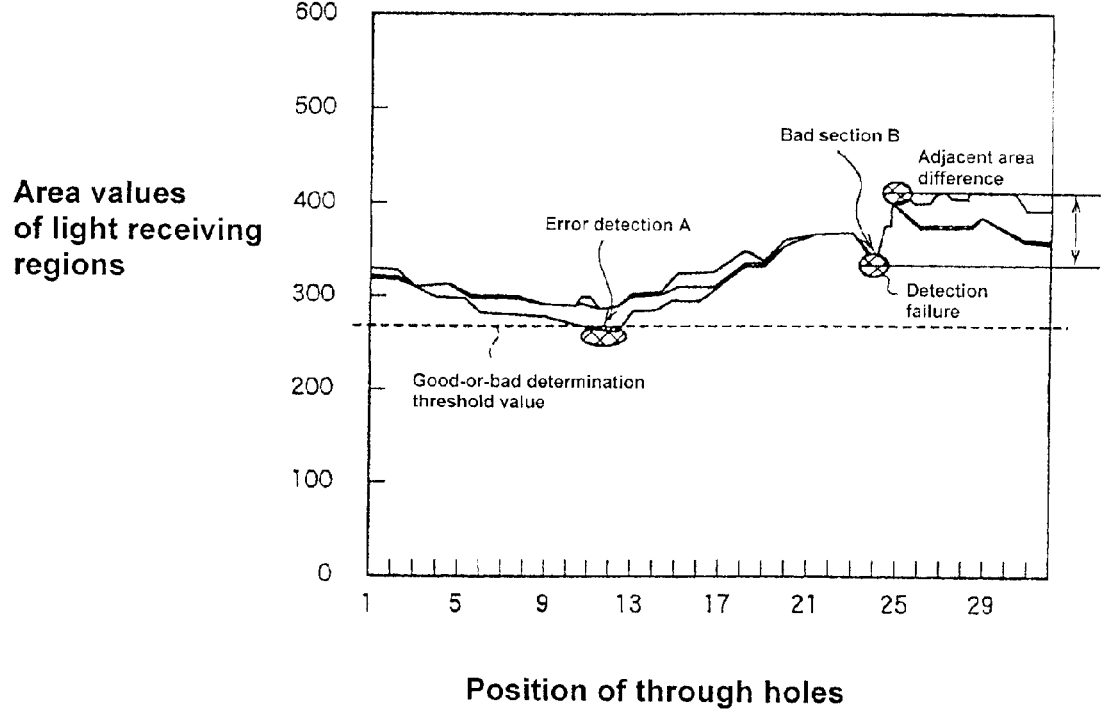
FIG. 10 is a graph showing a relation between locations of through holes of a work piece and area values thereof.

If area values of light receiving regions of the through holes 32 that are subject to the examination are extremely small, the foreign matter detection condition becomes stricter. As a result, due to individual conditions of work pieces that may be caused by, for example, bends in the work pieces, or at each time an image is taken, variations in the areas of the light receiving regions corresponding to the respective through holes occur. Therefore, if absolute threshold values are set for good-or-bad determination, the following problems may occur. As shown in FIG. 10, a determination may be made that an area value is small even though a foreign matter is not present, and error detection is made (at a section A in FIG. 10). On the other hand, a defective portion may not be detected because an area value of the light receiving region is large even though it is defective (at a section B in FIG. 10). Accordingly, in accordance with the embodiment of the present invention, area values of the light receiving regions corresponding to adjacent ones of the through holes 32 are compared. As a result, a stable examination without error detection can be conducted, and without being influenced by so-called tendency values such as bend of work pieces.

The determination process is conducted in a forward direction from No. 1 to No. n (step 620), and then the determination process is conducted in a reverse direction from No. n to No. 1 (step 630). Then, ANDs (logical products) of the measured results in the forward direction and the reverse direction are obtained for a final good-or-bad determination (step 640). Even when a plurality of through holes 32 that are subject to the examination are not arranged in a line, they can be similarly processed if the examined objects within the same examination range have a uniform size. In this case, a labeling function of the image processing device can be used, such that area differences among light receiving regions are obtained in the labeled order. The labeling is conducted by numbering them in order based on their coordinates.

Figure 11:
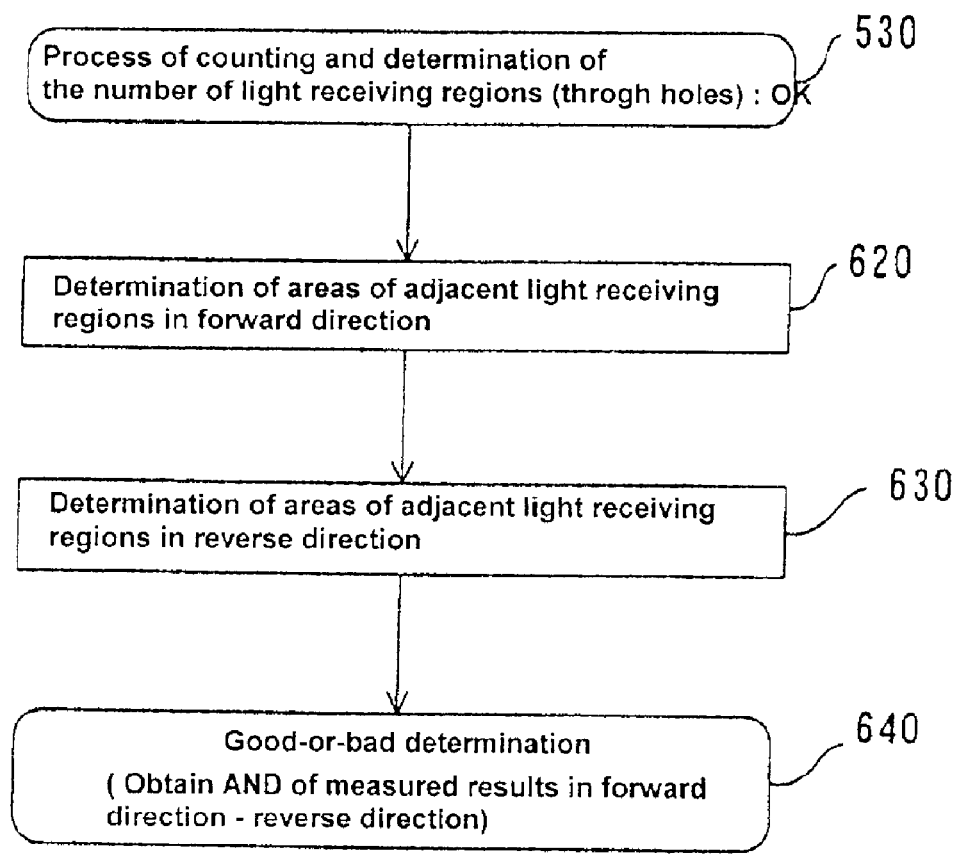
FIG. 11 is a basic flow chart of an adjacent area determination process.
Figure 12:
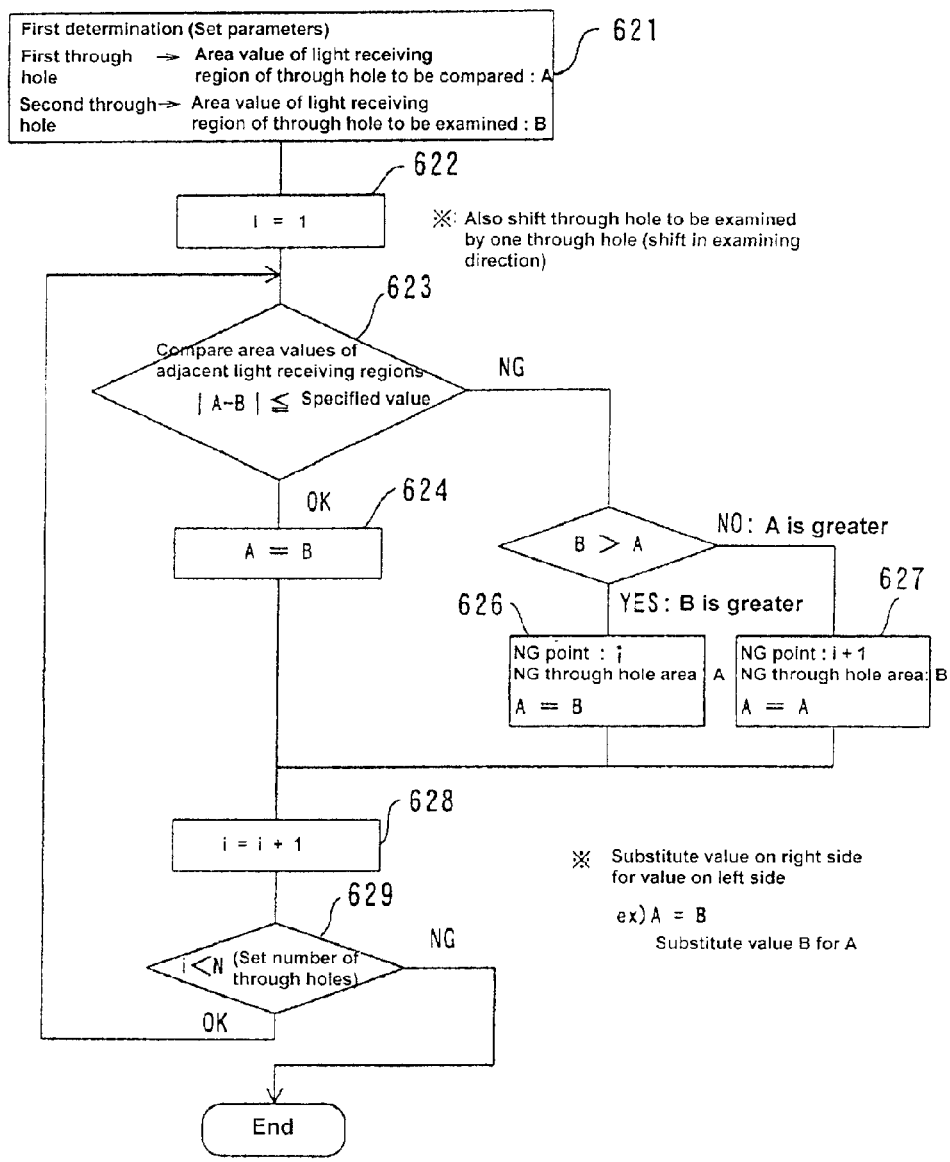
FIG. 12 is a flow chart of a concrete process to determine adjacent areas in the flow chart shown in FIG. 11.
Figure 14:
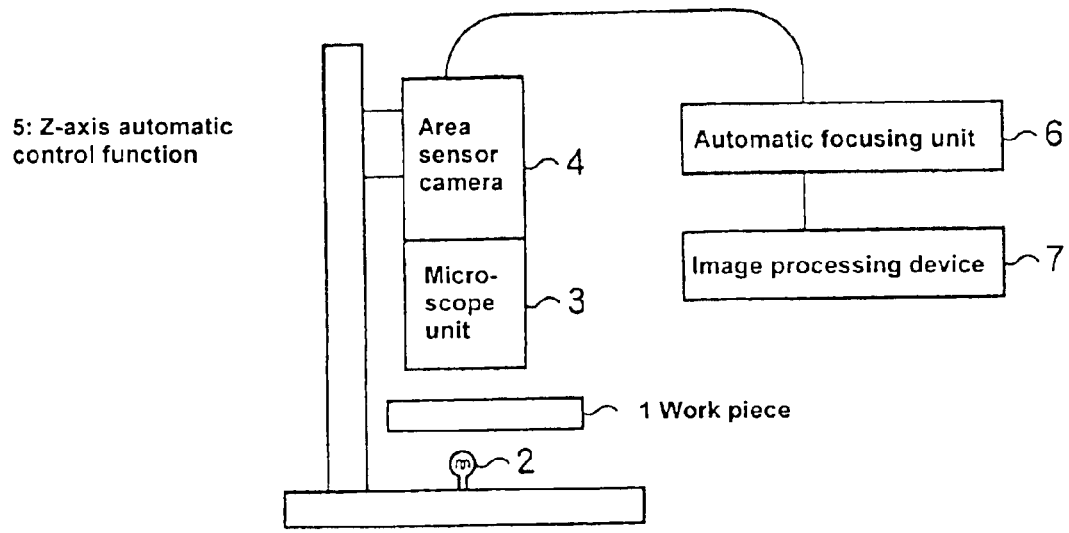
FIG. 14 shows a composition of a conventional foreign matter examination apparatus.
Figure 15:
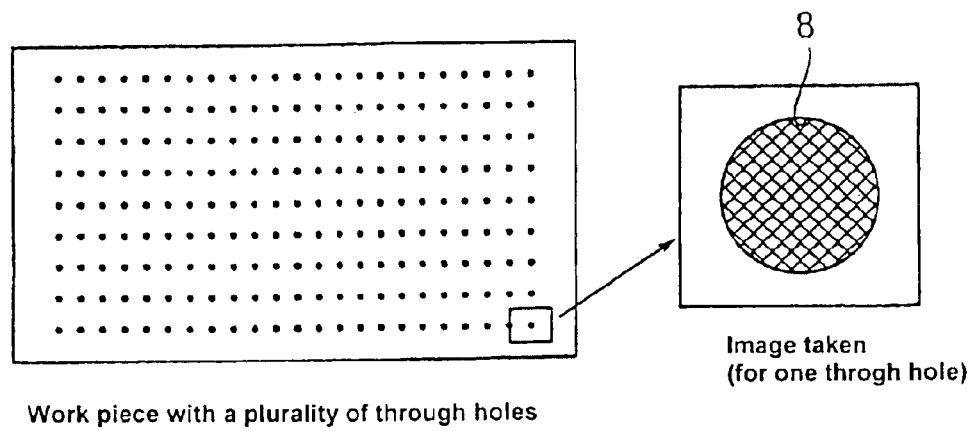
FIG. 15 is an illustration to describe examinations by the conventional apparatus.

A flow of the adjacent area determination process is shown in FIG. 11. The process is started (step 530) for a work piece 10 as an area determination object that is determined as "acceptable" in the initial step of the process to count and determine the number of light receiving regions (through holes) (step 500). In accordance with the embodiment of the present invention, an examination object in which the through holes are arranged in one column is subject to the examination. In this case, a labeling (numbering) function of the image processing device 24 is used. FIG. 12 shows a process flow of a concrete example of the determination of areas of light receiving regions corresponding to adjacent ones of the through holes. Area values of the light receiving regions corresponding to the plural through holes within an examination region in the image taken by scanning the work piece 10 are obtained. Initially, a parameter is set for the first determination (step 621). An area value of the light receiving region for the through hole No. 1 is set as a parameter A that is defined as an area value of the light receiving region of a through hole to be compared, and an area value of the light receiving region for the adjacent through hole No. 2 that is an object to be examined is set as a parameter B. A variable is set for the next examination to shift the light receiving regions corresponding to the through holes that are subject to the examination (step 622). Then, areas of the light receiving regions of the adjacent through holes 32 are mutually compared (step 623). In this comparison process, a difference of the areas of the light receiving regions (A–B) is compared with a specified value, and a determination is made by the following formula:

$$|A-B| \leq \text{Specified value}$$

The specified value may be determined based on the size of the through hole 32, the size of a foreign matter, or the like.

When the area value difference of the light receiving regions is within the specified value, the through hole A is determined as a good one, and at the same time, the parameter B is changed as parameter A. (step 624). When the area value difference of the light receiving regions exceeds the specified value, the area values for A and B are compared (step 625), one of the through holes that corresponds to a light receiving region with a smaller area value is determined as a bad through hole. This is because, when a foreign matter is present, the area value of light receiving region becomes smaller. In the case of A<B, an unacceptable (NG) point is A, and the point B is renewed as a light receiving region area value of the through hole that is subject to the next comparison (step 626). In the case of A>B, an unacceptable (NG) point is B, and the point A is continuously maintained as a light receiving region area value of the through hole that is subject to the next comparison (step 627). Then, the light receiving regions of the through holes that are subject to the examination are shifted (step 628). The above steps are repeated until the number of the through holes reaches a specified number of the through holes (step 629).

The determination process for determining areas of the light receiving regions of the adjacent through holes is conducted for the column of the through holes in the forward direction and in the reverse direction. The measured results are shown in Table 1 and Table 2 below. These results are obtained for the case in which there are 13 through holes, and a determination is made with the specified value being set at 100. Table 1 shows the results in the case of the forward direction, and Table 2 shows the results in the case of the reverse direction. Also, FIG. 13(1) is a graph showing positions of the through holes and area values of the light receiving regions of the through holes in the forward direction, and FIG. 13(2) shows that in the reverse direction.

TABLE 1

<<Determination of adjacent areas in the forward direction>>

| Position of through hole | Area value of light receiving region (B) | Area value of light receiving region to be compared (A) | Position of through hole to be compared | Area difference | Determination |
|---|---|---|---|---|---|
| 1 | 143 | — | — | — | OK |
| 2 | 150 | 143 | 1 | 7 | OK |
| 3 | 143 | 150 | 2 | 7 | NG |
| 4 | 304 | 143 | 3 | 161 | OK |
| 5 | 306 | 304 | 4 | 2 | OK |
| 6 | 307 | 306 | 5 | 1 | OK |
| 7 | 184 | 307 | 6 | 123 | NG |
| 8 | 200 | 307 | 6 | 107 | NG |
| 9 | 305 | 307 | 6 | 2 | OK |
| 10 | 310 | 305 | 9 | 5 | OK |
| 11 | 312 | 310 | 10 | 2 | OK |
| 12 | 308 | 312 | 11 | 4 | OK |
| 13 | 200 | 308 | 12 | 108 | NG |

TABLE 2

<<Determination of adjacent areas in the forward direction>>

| Position of through hole | Area value of light receiving region (B) | Area value of light receiving region to be compared (A) | Position of through hole to be compared | Area difference | Determination |
|---|---|---|---|---|---|
| 13 | 200 | — | — | — | NG |
| 12 | 308 | 200 | 13 | 108 | OK |
| 11 | 312 | 308 | 12 | 4 | OK |
| 10 | 310 | 312 | 11 | 2 | OK |
| 9 | 305 | 310 | 10 | 5 | OK |
| 8 | 200 | 305 | 9 | 105 | NG |
| 7 | 184 | 305 | 9 | 121 | NG |
| 6 | 307 | 305 | 9 | 2 | OK |
| 5 | 306 | 307 | 6 | 1 | OK |
| 4 | 304 | 306 | 5 | 2 | OK |
| 3 | 143 | 304 | 4 | 161 | NG |
| 2 | 150 | 304 | 4 | 154 | NG |
| 1 | 143 | 304 | 4 | 161 | NG |

In Table 1, when the through hole position No. 2 is initially subject to the examination (as being B), and No.

1(A) and No. 2(B) are compared, an area difference thereof is within the specified value, and therefore a determination is made that No. 1 is acceptable (OK). When the through hole position No. 3 is subject to the examination, and No. 2 and No. 3 are compared, an area difference thereof is within the specified value, and therefore a determination is made that No. 2 is acceptable (OK). In the case of No. 3 and No. 4, an area difference is 161 in which the area value of No. 4 is greater, and a determination is made that No. 4 is acceptable (OK), and No. 3 is not acceptable (NG). Also, for example, when the through hole position No. 7 is subject to the examination, No. 7 is determined to be unacceptable (NG) because the through hole No. 6 that is subject to a comparison has a light receiving region area corresponding thereto is larger (A>B), and No. 6 is made subject to the next comparison. The process and determination are similarly conducted for the other through holes. Also, in the determinations in the reverse direction shown in Table 2, a difference obtained in comparison between No. 13 (as being B) and No. 12 (as being A) is 108, in other words, B>A. Accordingly, in step 626, No. 13 is determined to be unacceptable (NG), and No. 12 is determined to be acceptable (OK). By performing these processes, the determination results in the forward direction and the reverse direction shown in Table 1 and Table 2 are obtained.

The determination process is used to make a final good-or-bad determination for through hole positions. As shown in step 640 (FIG. 11), ANDs (logical products) of the measured results in the forward direction and the reverse direction are obtained to make a final good-or-bad determination. Results of the determination process are shown in the next table.

to about 300 through holes is taken in a lot, the efficiency is substantially high. Also, since an image is taken with the position of the focal point of the line sensor camera 14 being shifted, a transparent foreign matter in a through hole can create a large difference in the light receiving region area compared to a normal through hole, such that the comparison and determination can be readily made. The size (area) of a detectable transparent foreign matter is 15% or greater than a light receiving region area of a reference through hole. It is noted that, if foreign matters are colored, much smaller sized foreign matters can be detected.

In determination of foreign matters, a determination is initially made to confirm if light receiving regions within an examination range are present in the same number as a specified number of through holes. As a result, the occurrence of detection failures in the process of determining areas of light receiving region areas of adjacent through holes in the second determination process. When the light receiving regions are not recognized as being in the number equal to the specified number of through holes, the examination process for the work piece 10 is stopped. Therefore, the process load in the image processing device 24 is alleviated. Differences in the areas of light receiving regions of adjacent through holes are obtained only for work pieces with a specified number of through holes. An area value of a light receiving region for each of the through holes is not compared, but area values of light receiving regions for adjacent through holes are compared with each other. As a result, error detection or detection failures that may be caused by bends of work pieces do not occur.

It is noted that, by examining under an out-of-focus condition, the conditions for examining foreign matters may

TABLE 3

Good-or-bad determination for through hole positions

| | 1 | 2 | 3 | 4 | 5 | 6 | 7 | 8 | 9 | 10 | 11 | 12 | 13 |
|---|---|---|---|---|---|---|---|---|---|---|---|---|---|
| Forward direction | OK | OK | NG | OK | OK | OK | NG | NG | OK | OK | OK | OK | NG |
| Reverse direction | NG | NG | NG | OK | OK | OK | NG | NG | OK | OK | OK | OK | NG |
| AND determination | NG | NG | NG | OK | OK | OK | NG | NG | OK | OK | OK | OK | NG |

In this manner, good-or-bad determinations are made for each of the forward direction and the reverse direction, and ANDs of these results are obtained. As a result, a good-or-bad determination for the through hole that is located at the start of the examination and the last through hole can be correctly made.

By the method and apparatus for examining foreign matters in through holes in accordance with the embodiment of the present invention, for example, a line sensor camera 14 is scanned across a work piece 10 having a plurality of through holes to take an image of a region including a plurality of examination ranges in a lot. The number of light receiving regions and areas of the light receiving regions are obtained based on light passing through the through holes for each of the examination regions that are set in the image taken. As a result, the processing speed is substantially increased compared to an examination process in which each and every through hole is compared. In other words, an image of a wide range is taken, and a plurality of through holes are processed in a lot. Although depending on the shape of work pieces, currently, image data that corresponds become strict, and deviations may occur in area values of light receiving regions for the through holes among different work pieces or at each time an image is taken. Therefore, if area values of light receiving regions for through holes are simply compared with reference area values as threshold values to make good-or-bad determinations, there may be possibilities of detection errors and detection failures. However, by conducting the process in which area values of light receiving regions of adjacent through holes are compared with each other, stable examinations can be conducted.

It is noted that the above-described method is also applicable to a composition in which an area sensor is used instead of a line sensor. Such an apparatus composition can be realized by mounting an area sensor camera instead of the line sensor camera 14 shown in FIG. 1. When a work piece 14 is imaged using the area sensor camera, each through hole 32 may be imaged as one unit. However, for a quicker process, a plurality of through holes in a group may preferably be taken in a lot as image data. The area sensor camera receives light passing through the through holes 32, light receiving regions of the respective through holes 32 are binarized, and area values of the light receiving regions are obtained by counting imaging elements in each of the regions. In this manner, an area of each of the light receiving regions for the respective through holes 32 is determined as one mass, and the number of the areas is obtained. The number is compared with a reference through hole number to make a good-or-bad determination. Then, the area values of the light receiving regions corresponding to the respective through holes 32 are compared with one another, wherein the presence or the absence of foreign matters can be determined. This determination process can be conducted in the same manner as conducted for image data that is taken by the line sensor camera 14 described above.

In accordance with the embodiment described above, the following effects are obtained. Namely, the line sensor camera 14 may not necessarily be required, but an area sensor camera may be used, whereby the sizes of the light receiving regions are compared with one another in a similar manner described above, and a determination can be accurately made as to whether a foreign matter is present in the through holes 32. Even when work pieces 10 are bent, foreign matters can be examined with high accuracy with a simple facility structure compared to the conventional method.

What is claimed is:

1. A method for examining foreign matters in through holes formed in a work piece, the method characterized in that light passing through a plurality of through holes having a uniform size is taken as image data by relative movement between the work piece and a line sensor camera, and sizes of regions that receive individual passing light in the image data are mutually compared to determine presence or absence of foreign matter.

2. A method for examining foreign matters in through holes according to claim 1, wherein after counting and determining a number of areas of light receiving regions corresponding to the through holes, the areas of light receiving regions are mutually compared.

3. A method for examining foreign matters in through holes according to claim 1, wherein areas of light receiving regions are labeled and the labeled areas of light receiving regions are mutually compared to determine presence or absence of foreign matter.

4. A method for examining foreign matters in through holes according to claim 1, wherein said step of mutually comparing sizes of regions that receive individual passing light in the image data is based on magnitudes of differences in light receiving regions of adjacent ones of the through holes to determine presence or absence of foreign matter.

5. An apparatus for examining foreign matters in through holes, the apparatus comprising:
   a light source provided on one side of a work piece and a line sensor camera provided on the other side of the work piece, the work piece having a plurality of through holes;
   a parallel displacement system that translates the work piece and the line sensor camera relative to each other to allow the line sensor camera to detect light passing through the plurality of through holes in one lot; and
   an image processing device that receives detected signals provided by the line sensor camera to obtain a plurality of binary image data corresponding to the plurality of through holes in the work piece,
   wherein the image processing device is equipped with a determination device that makes a determination as to whether foreign matter is present or absent in the through holes based on deviations among receiving light regions corresponding to the respective through holes.

* * * * *